(12) United States Patent
Muller et al.

(10) Patent No.: US 8,545,487 B2
(45) Date of Patent: Oct. 1, 2013

(54) EYE THERAPY SYSTEM

(75) Inventors: David Muller, Boston, MA (US);
Thomas Ryan, Waltham, MA (US)

(73) Assignee: Avedro Inc., Waltham, MA (US)

( * ) Notice: Subject to any disclaimer, the term of this patent is extended or adjusted under 35 U.S.C. 154(b) by 1241 days.

(21) Appl. No.: 12/315,829

(22) Filed: Dec. 5, 2008

(65) Prior Publication Data

US 2009/0149842 A1 Jun. 11, 2009

Related U.S. Application Data

(60) Provisional application No. 60/992,486, filed on Dec. 5, 2007, provisional application No. 61/098,489, filed on Sep. 19, 2008, provisional application No. 61/101,509, filed on Sep. 30, 2008.

(51) Int. Cl.
*A61B 17/22* (2006.01)

(52) U.S. Cl.
USPC .............................. 606/5; 128/898

(58) Field of Classification Search
USPC .................. 606/5, 32, 41; 128/898
See application file for complete search history.

(56) References Cited

U.S. PATENT DOCUMENTS

| | | |
|---|---|---|
| 4,034,750 A | 7/1977 | Seiderman |
| 4,161,013 A | 7/1979 | Grodzinsky et al. |
| 4,326,529 A | 4/1982 | Doss et al. |
| 4,381,007 A | 4/1983 | Doss |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,994,058 A | 2/1991 | Raven et al. |
| 5,016,615 A | 5/1991 | Driller et al. |
| 5,019,074 A * | 5/1991 | Muller .............................. 606/5 |
| 5,103,005 A | 4/1992 | Gyure et al. |
| 5,171,254 A | 12/1992 | Sher |

(Continued)

FOREIGN PATENT DOCUMENTS

| | | |
|---|---|---|
| EP | 1 561 440 A1 | 8/2005 |
| EP | 1 790 383 A1 | 5/2007 |

(Continued)

OTHER PUBLICATIONS

Berjano et al.; "Radio-Frequency Heating of the Cornea: Theoretical Model and in Vitro Experiments"; IEEE Transactions on Biomedical Engineering; vol. 49; No. 3; Mar. 2002; pp. 196-205.

(Continued)

*Primary Examiner* — Victor Nguyen
(74) *Attorney, Agent, or Firm* — Nixon Peabody LLP

(57) ABSTRACT

Heat is generated in corneal fibrils in a cornea of an eye according to a selected pattern. The heat causes the corneal fibrils corresponding to the selected pattern to transition from a first structure to a second structure. The second structure provides a desired reshaping of the cornea. A cross-linking agent is then activated in the region of corneal fibrils according to the selected pattern. The cross-linking agent prevents the corneal fibrils from changing from the second structure. Thus, embodiments stabilize corneal tissue and improve its biomechanical strength after desired structural changes have been achieved in the corneal tissue. Accordingly, the embodiments help to preserve the desired reshaping of the cornea.

13 Claims, 11 Drawing Sheets

(56) References Cited

U.S. PATENT DOCUMENTS

| | | | |
|---|---|---|---|
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,618,284 A | 4/1997 | Sand |
| 5,634,921 A | 6/1997 | Hood et al. |
| 5,766,171 A | 6/1998 | Silvestrini |
| 5,779,696 A | 7/1998 | Berry et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,223,075 B1 | 4/2001 | Beck et al. |
| 6,293,938 B1 | 9/2001 | Muller |
| 6,319,273 B1 | 11/2001 | Chen et al. |
| 6,325,792 B1 | 12/2001 | Swinger et al. |
| 6,334,074 B1 | 12/2001 | Spertell |
| 6,342,053 B1 | 1/2002 | Berry |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 * | 3/2003 | Karageozian et al. ....... 424/94.4 |
| 6,572,849 B2 | 6/2003 | Shahinian, Jr. |
| 6,617,963 B1 | 9/2003 | Watters et al. |
| 6,918,904 B1 | 7/2005 | Peyman |
| 6,946,440 B1 | 9/2005 | DeWoolfson et al. |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,270,658 B2 | 9/2007 | Woloszko et al. |
| 7,331,350 B2 | 2/2008 | Kochevar et al. |
| 7,402,562 B2 | 7/2008 | DeWoolfson |
| 7,753,943 B2 * | 7/2010 | Strong ............................ 607/88 |
| 2001/0041856 A1 | 11/2001 | McDaniel |
| 2002/0002369 A1 | 1/2002 | Hood |
| 2002/0013577 A1 | 1/2002 | Frey et al. |
| 2002/0049437 A1 | 4/2002 | Silvestrini |
| 2002/0099363 A1 | 7/2002 | Woodward et al. |
| 2002/0164379 A1 | 11/2002 | Nishihara et al. |
| 2003/0018255 A1 | 1/2003 | Martin et al. |
| 2003/0175259 A1 | 9/2003 | Karageozian et al. |
| 2003/0216728 A1 | 11/2003 | Stern et al. |
| 2004/0001821 A1 | 1/2004 | Silver et al. |
| 2004/0071778 A1 | 4/2004 | Bellmann et al. |
| 2004/0093046 A1 | 5/2004 | Sand |
| 2004/0111086 A1 | 6/2004 | Trembly |
| 2004/0143250 A1 | 7/2004 | Trembly |
| 2004/0199158 A1 | 10/2004 | Hood et al. |
| 2004/0204707 A1 | 10/2004 | Hood et al. |
| 2004/0243160 A1 | 12/2004 | Shiuey et al. |
| 2005/0038471 A1 | 2/2005 | Chan et al. |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0276777 A1 | 12/2006 | Coroneo |
| 2006/0287662 A1 | 12/2006 | Berry et al. |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203547 A1 | 8/2007 | Costello et al. |
| 2007/0244470 A1 | 10/2007 | Barker et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0234335 A1 | 9/2009 | Yee |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | De Juan, Jr. et al. |
| 2010/0057060 A1 | 3/2010 | Herekar |
| 2010/0069894 A1 | 3/2010 | Mrochen et al. |
| 2010/0082018 A1 | 4/2010 | Panthakey |
| 2010/0094197 A1 | 4/2010 | Marshall et al. |
| 2010/0114109 A1 | 5/2010 | Peyman |
| 2010/0149842 A1 | 6/2010 | Muller et al. |
| 2010/0173019 A1 | 7/2010 | Paik et al. |
| 2010/0189817 A1 | 7/2010 | Krueger et al. |
| 2010/0210996 A1 | 8/2010 | Peyman |
| 2010/0286156 A1 | 11/2010 | Pinelli |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0208300 A1 | 8/2011 | Eugene et al. |
| 2011/0237999 A1 | 9/2011 | Muller et al. |
| 2011/0264082 A1 | 10/2011 | Mrochen |
| 2011/0301524 A1 | 12/2011 | Bueler |

FOREIGN PATENT DOCUMENTS

| | | |
|---|---|---|
| EP | 2 253 321 A1 | 11/2010 |
| IT | MI2010A001236 | 5/2010 |
| WO | 00/74648 A2 | 12/2000 |
| WO | WO 2004/052223 A2 | 6/2004 |
| WO | WO 2005/110397 A1 | 11/2005 |
| WO | WO 2006/012947 A2 | 2/2006 |
| WO | 2006128038 A2 | 11/2006 |
| WO | WO 2007/001926 A2 | 1/2007 |
| WO | 2007/120457 A2 | 10/2007 |
| WO | WO 2007/143111 A2 | 12/2007 |
| WO | WO 2008/000478 A1 | 1/2008 |
| WO | WO 2009/146151 A2 | 12/2009 |
| WO | WO 2010/011119 A1 | 1/2010 |
| WO | WO 2010/023705 A1 | 3/2010 |

OTHER PUBLICATIONS

Berjano et. al.; "Ring Electrode for Radio-Frequency Heating of the Cornea: Modelling and in Vitro Experiments"; Medical & Biological Engineering & Computing 2003; vol. 41; pp. 630-639.

International Search Report mailed Aug. 14, 2009 for PCT/US2009/042204, (5 pages).

International Search Report mailed Nov. 20, 2009 for PCT/2009/059061 (3 pages).

International Search Report mailed Nov. 6, 2009 for PCT/US2009/057481 (2 pages).

International Search Report for PCT/US08/013426, dated Feb. 2, 2009.

Written Opinion of the International Searching Authority for PCT/US08/013426, dated Feb. 2, 2009.

Muller et al., Br. J. Opthalmol 2001; 85:437-443 (April).

Naoumidi et al., J. Cataract Refract Surg. May 2006; 32(5):732-41.

Pallikaris et al., J. Cataract Refract Surg. Aug. 2005; 31(8):1520-29.

Acosta et al., Cornea. Aug. 2006;25(7):830-8.

Chandonnet, CO2 Laser Annular Thermokeratoplasty: A Preliminary Study, Lasers in Surgery and Medicine 12:264-273 (1992), Wiley-Lill, Inc.

International Search Report for PCT/US2010/029806 dated Jun. 1, 2010 (3 pages).

Written Opinion for PCT/US2010/029806 dated Jun. 1, 2010 (6 pages).

International Search Report for PCT/US2010/029791 dated Jun. 1, 2010 (3 pages).

Written Opinion for PCT/US2010/029791 dated Jun. 1, 2010 (6 pages).

Trembly et al.; Microwave Thermal Keratoplasty for Myopia: Keratoscopic Evaluation in Procine Eyes; Journal of Refractive Surgery; vol. 17; Nov./Dec. 2001; (8 pages).

Baier J. et al., "Singlet Oxygen Generation by UVA Light Exposure of Endogenous Photosensitizers," *Biophysical Journal*, vol. 91(4), pp. 1452-1459; Aug. 15, 2006 (8 pages).

Chan B.P., et al., "Effects of photochemical crosslinking on the microstructure of collagen and a feasibility study on controlled protein release;" *Acta Biomaterialia*, vol. 4, Issue 6, pp. 1627-1636; Jul. 1, 2008 (10 pages).

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).

Corbett M., et al., "Effect of Collagenase Inhibitors on Corneal Haze after PRK," *Exp. Eye Res.*, vol. 72, Issue 3, pp. 253-259; Jan. 2001 (7 pages).

Coskenseven E. et al., "Comparative Study of Corneal Collagen Cross-linking With Riboflaving and UVA Irradiation in Patients With Keratoconus," *Journal of Refractive Surgery*, vol. 25, issue 4, pp. 371-376; Apr. 2009 (6 pages).

"Definity (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011 (15 pages).

Ehlers W., et al., "Factors Affecting Therapeutic Concentration of Topical Aminocaproic Acid in Traumatic Hyphema," *Investigative Ophthalmology & Visual Science*, vol. 31, No. 11, pp. 2389-2394; Nov. 1990 (6 pages).

Erskine H., "Avedro Becomes Sponsor of US FDA Clinical Trials of Corneal Collagen Crosslinking," Press Release, Mar. 16, 2010 (1 page).

Glenn J.V., et al., "Advanced Glycation End Product (AGE) Accumulation on Bruch's Membrane: Links to Age-Related RPE Dysfunction;" *Investigative Ophthalmology & Visual Science*, vol. 50, No. 1, pp. 441-451; Jan. 2009 (11 pages).

Gravitz L., "Laser Show in the Surgical Suite: Lasers and a century-old dye could supplant needles and thread;" *technology review*, MIT, Mar./Apr. 2009; retrieved from http://www.technologyreview.com/biomedicine/22088/?nlid=1767, on Sep. 26, 2011 (2 pages).

Hafezi F., et al., "Collagen Crosslinking with Ultraviolet-A and Hypoosmolar Riboflavin Solution in Thin Corneas," *J. Catract Refract. Surg.*, vol. 35, No. 1, pp. 621-624; Apr. 2009 (4 pages).

How to Use Definity: "Frequently Asked Questions;" retrieved from http://www.definityimaging.com/how-faq.html, on Sep. 26, 2011 (3 pages) (date unknown, prior to Apr. 26, 2010).

Imex, "KXL System: Crosslinking Para Cirugia Corneal Bibliografia Cientifica," Product Literature, Nov. 23, 2010 (24 pages).

Kampik D. et al., "Influence of Corneal Collagen Crosslinking With Riboflavin and Ultraviolet-A Irradiation on Excimer Laser Surgery," *Investigative Opthalmology & Visual Science*, vol. 51, No. 8, pp. 3929-3934; Aug. 2010 (6 pages).

Kissner Anja, et al., "Pharmacological Modification of the Epithelial Permeability by Benzalkonium Chloride in UVA/Riboflavin Corneal Collagen Cross-Linking," *Current Eye Research* 35(8), pp. 715-721; Mar. 2010 (7 pages).

Koller T., et al., "Therapeutische Quervernetzung der Hornhaut mittels UVA und Riboflavin: Therapeutic Cross-Linking of the Cornea Using Riboflavin/UVA," *Klinische Monatsblätter für Augenheilkunde*, vol. 224, No. 9, pp. 700-706; Sep. 2007 (7 pages).

Krueger, Ronald R., "Rapid VS Standard Collagen CXL with Equivalent Energy Dosing," presentation slides, (26 pages); available at http://www.slideshare.net/logen/krueger-herekar-rapid-cross-linking (date unknown, prior to Nov. 9, 2009).

Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).

Mulroy L., et al., "Photochemical Keratodesmos for repair of Lamellar corneal Incisions;" *Investigative Ophthalmology & Visual Science*, vol. 41, No. 11, pp. 3335-3340; Oct. 2000 (6 pages).

O'Neil A.C., et al., "Microvascular Anastomosis Using a Photochemical Tissue Bonding Technique;" *Lasers in Surgery and Medicine*, vol. 39, Issue 9, pp. 716-722; Oct. 2007 (7 pages).

Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).

Pinelli R., et al., "C3-Riboflaving Treatments: Where Did We Come From? Where Are We Now?" *Cataract & Refractive Surgery Today Europe*, Summer 2007, pp. 36-46; Jun. 2007 (10 pages).

Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," *J. Cataract Refract. Surgery*, vol. 35, No. 6, pp. 1055-1062; Jun. 2009 (8 pages).

Proano C.E., et al., "Photochemical Keratodesmos for Bonding Corneal Incisions;" *Investigative Ophthalmology & Visual Science*, vol. 45, No. 7, pp. 2177-2181; Jul. 2004 (5 pages).

Rocha K., et al., "Comparative Study of Riboflavin-UVA Cross-linking and "Flash-linking" Using Surface Wave Elastometry," *Journal of Refractive Surgery*, vol. 24 Issue 7, pp. S748-S751; Sep. 2008 (4 pages).

RxList: "Definity Drug Description;" *The Internet Drug Index*, revised Jun. 16, 2008, retrieved from http://www.rxlist.com/definity-drug.htm, on Sep. 26, 2011 (4 pages).

Sheehan M., et al., "Illumination System for Corneal Collagen Crosslinking," *Optometry and Vision Science*, vol. 88, No. 4, pp. 512-524; Apr. 2011 (13 pages).

Shell, J., "Pharmacokinetics of Topically Applied Ophthalmic Drugs," *Survey of Ophthalmology*, vol. 26, No. 4, pp. 207-218; Jan.-Feb. 1982 (12 pages).

Sonoda S., "Gene Transfer to Corneal Epithelium and Keratocytes Mediated by Ultrasound with Microbubbles," *Investigative Ophthalmology & Visual Science*, vol. 47, No. 2, pp. 558-564; Feb. 2006 (7 pages).

Spoerl E., et al., "Artificial Stiffening of the Cornea by Induction of Intrastromal Cross-links," *Der Ophthalmologe*, vol. 94, No. 12, pp. 902-906; Dec. 1997 (5 pages).

Spoerl E., et al., "Induction of Cross-links in Corneal Tissue," *Experimental Eye Research*, vol. 66, Issue 1, pp. 97-103; Jan. 1998 (7 pages).

Spoerl E., et al., "Techniques for Stiffening the Cornea," *Journal of Refractive Surgery*, vol. 15, Issue 6, pp. 711-713; Nov.-Dec. 1999 (4 pages).

Spoerl E. et al., "Safety of UVA-Riboflavin Cross-Linking of the Cornea," *Cornea*, vol. 26, No. 4, pp. 385-389; May 2007 (5 pages).

Tessier Fj, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).

"UV-X: Radiation System for Treatment of Keratokonus," *PESCHKE Meditrade GmbH*; retrieved from http://www.peschkemed.ch/ on Sep. 27, 2011 (1 page) (date unknown, prior to Sep. 16, 2008).

Vasan S., et al., "An agent cleaving glucose-derived protein crosslinks in vitro and in vivo;" *Letters to Nature*, vol. 382, pp. 275-278; Jul. 18, 1996 (4 pages).

Wollensak G., et al., "Collagen Crosslinking of Human and Porcine Sclera," *J. Cataract Refract. Surg.*, vol. 30, Issue 3, pp. 689-695; Mar. 2004 (7 pages).

Wollensak G., et al., "Riboflavin/Ultraviolet-A-induced Collagen Crosslinking for the Treatment of Keratoconus," *American Journal of Ophthalmology*, vol. 135, No. 5, pp. 620-627; May 2003 (8 pages).

Wollensak G., et al., "Cross-linking of Scleral Collagen in the Rabbit Using Riboflavin and UVA," *Acta Ophtalmologica Scandinavica*, vol. 83(4), pp. 477-482; Aug. 2005 (6 pages).

Wollensak G., "Crosslinking Treatment of Progressive Keratoconus: New Hope," *Current Opinion in Ophthalmology*, vol. 17(4), pp. 356-360; Aug. 2006 (5 pages).

Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

Wollensak G., et al., "Biomechanical and Histological Changes After Corneal Crosslinking With and Without Epithelial Debridement," *J. Cataract Refract. Surg.*, vol. 35, Issue 3, pp. 540-546; Mar. 2009 (7 pages).

Yang H., et al., "3-D Histomorphometry of the Normal and Early Glaucomatous Monkey Optic Nerve Head: Lamina Cribrosa and Peripapillary Scleral Position and Thickness," *Investigative Ophthalmology & Visual Science*, vol. 48, No. 10, pp. 4597-4607; Oct. 2007 (11 pages).

Zderic V., et al., "Drug Delivery Into the Eye With the Use of Ultrasound," *J. Ultrasound Med*, vol. 23(10), pp. 1349-1359; Oct. 2004 (11 pages).

Zderic V., et al., "Ultrasound-enhanced Transcorneal Drug Delivery," *Cornea* vol. 23, No. 8, pp. 804-811; Nov. 2004 (8 pages).

Written Opinion and Supplemental European Search Report for European Application No. EP 08 855 817.6, mailed Jun. 10, 2011 (8 pages).

International Search Report and Written Opinion for International Patent Application No. PCT/US2008/013426, mailed Feb. 2, 2009 (6 pages).

Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969 (7 pages).

Brüel, A., "Changes in Biomechanical Properties, Composition of Collagen and Elastin, and Advanced Glycation Endproducts of the Rat Aorta in Relation to Age," Atherosclerosis 127, Mar. 14, 1996 (11 pages).

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).

Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).

Gibson, Q. et al., "The Oxidation of Reduced Flavin Mononucleotide by Molecular Oxygen," Biochem. J. (1962) 83, 368-377 (10 pages).

Holmström, B. et al., "Riboflavin as an Electron Donor in Photochemical Reactions," 1867-1871, Nov. 29, 1960 (5 pages).

Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).

Krueger, R. et al., "Rapid vs. Standard Collagen CXL With Equivalent Energy Dosing," posted Nov. 9, 2009 (26 pages).

Massey, V., "Activation of Molecular Oxygen by Flavins and Flavoproteins," The Journal of Biological Chemistry vol. 269, No. 36, Issue of Sep. 9, pp. 22459-22462, 1994 (4 pages).

Rolandi et al. Correlation of Collagen-Linked Fluorescence and Tendon Fiber Breaking Time. Gerontology 1991;27:240-243 (4 pages).

Song P., Metzler D. Photochemical Degradation of Flavins—IV. Studies of the Anaerobic Photolysis of Riboflavin. Photochemistry and Photobiology, vol. 6, pp. 691-709, 1967 (21 pages).

Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).

Hitzenberger et al., "Birefringence Properties of the Human Cornea Measured With Polarization Sensitive Optical Coherence Tomography," Bull. Soc. Beige Ophtalmol., 302, 153-168, 2006.

Frucht-Pery, et al. "Iontophoresis—gentamicin delivery into the rabbit cornea, using a hydrogel delivery probe," Jun. 20, 2003 (5 pages).

* cited by examiner

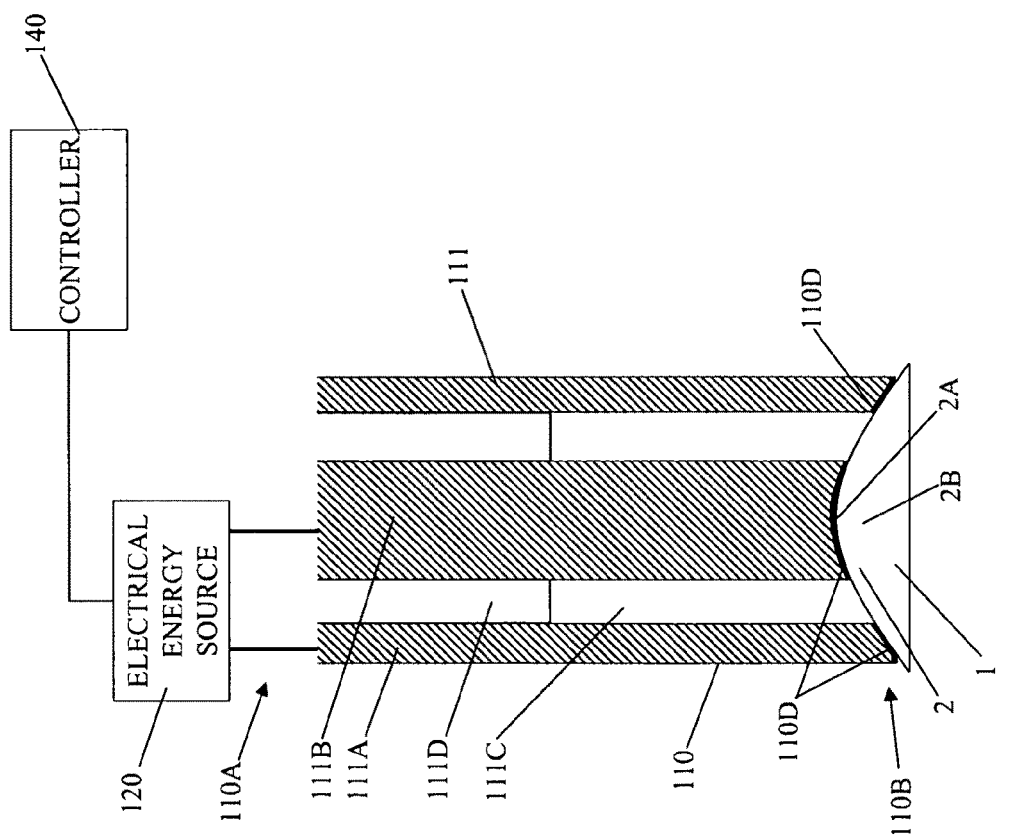

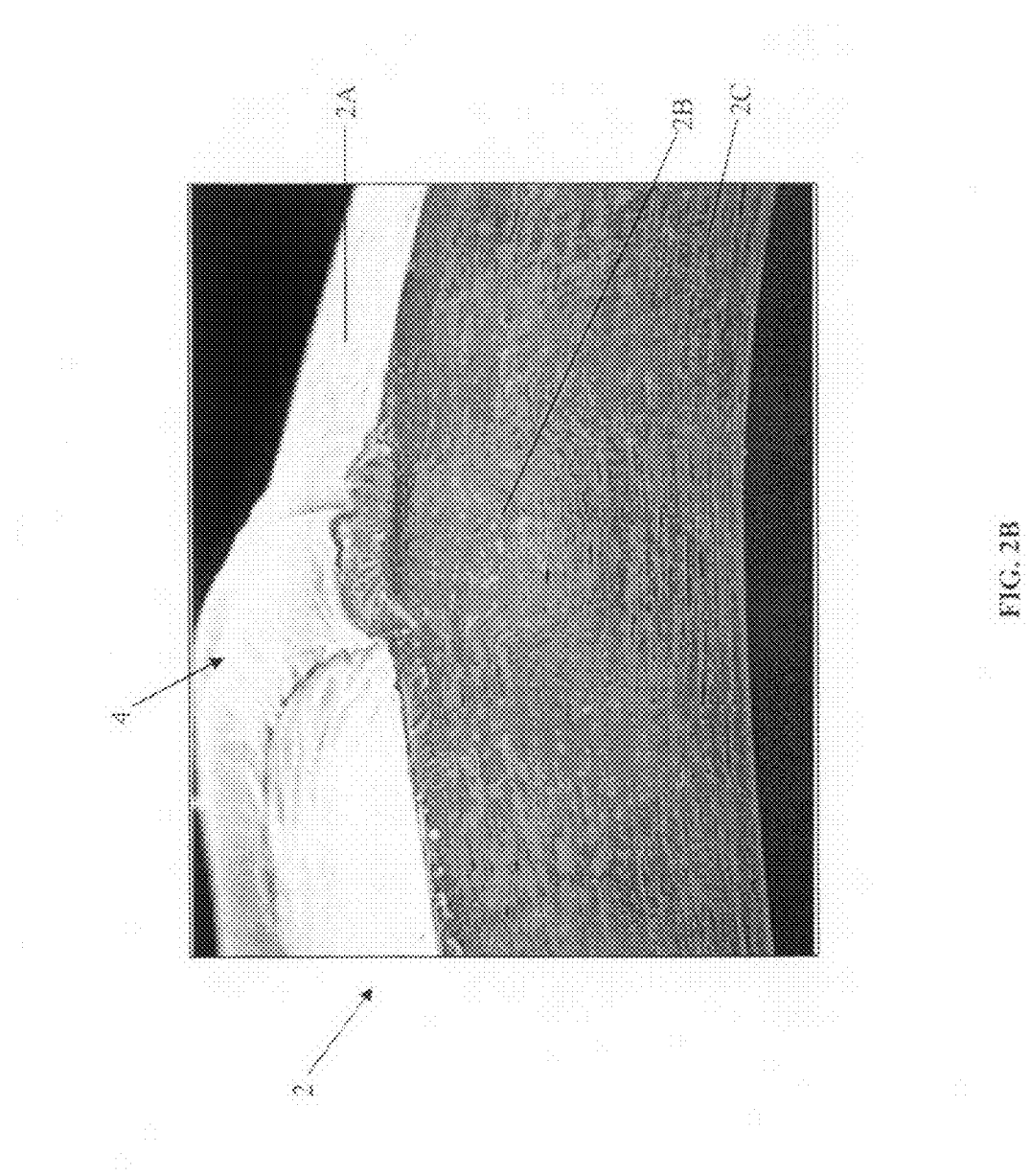

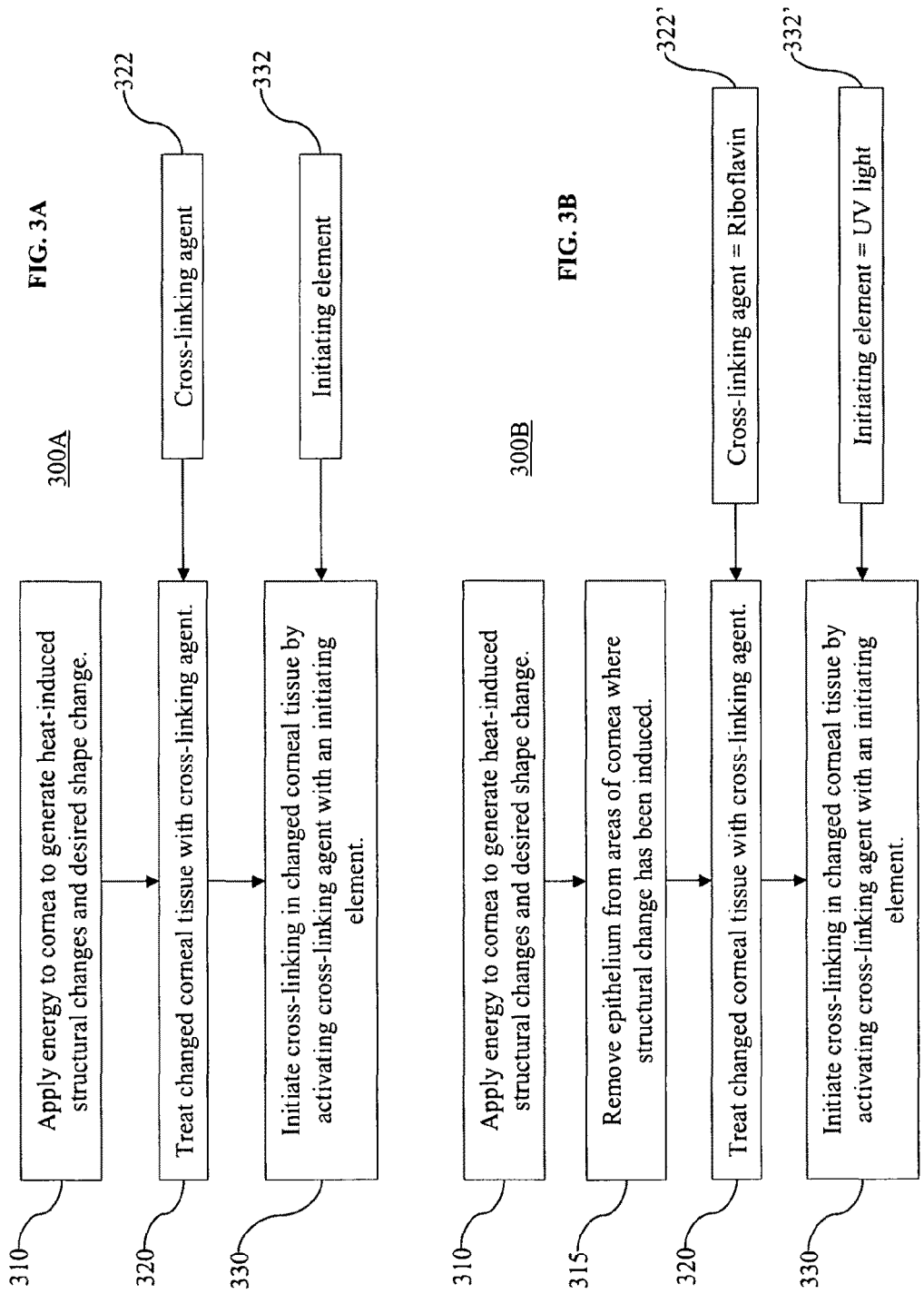

EYE THERAPY SYSTEM

CROSS REFERENCE TO RELATED APPLICATIONS

This application claims priority to U.S. Provisional Application No. 60/992,486, filed Dec. 5, 2007, U.S. Provisional Application No. 61/098,489, filed Sep. 19, 2008, and U.S. Provisional Application No. 61/101,509, filed Sep. 30, 2008, the contents of these applications being incorporated entirely herein by reference.

BACKGROUND OF THE INVENTION

1. Field of the Invention

The invention pertains to the field of keratoplasty and, more particularly, to systems and methods for stabilizing changes to corneal tissue after the application of energy to the corneal tissue.

2. Description of Related Art

A variety of eye disorders, such as myopia, keratoconus, and hyperopia, involve abnormal shaping of the cornea. Keratoplasty reshapes the cornea to correct such disorders. For example, with myopia, the shape of the cornea causes the refractive power of an eye to be too great and images to be focused in front of the retina. Flattening aspects of the cornea's shape through keratoplasty decreases the refractive power of an eye with myopia and causes the image to be properly focused at the retina.

Invasive surgical procedures, such as laser-assisted in-situ keratomileusis (LASIK), may be employed to reshape the cornea. However, such surgical procedures typically may require an extended healing period after surgery. Furthermore, such surgical procedures may involve complications, such as dry eye syndrome caused by the severing of corneal nerves.

Thermokeratoplasty, on the other hand, is a noninvasive procedure that may be used to correct the vision of persons who have disorders associated with abnormal shaping of the cornea, such as myopia, keratoconus, and hyperopia. Thermokeratoplasty may be performed by applying electrical energy in the microwave or radio frequency (RF) band. In particular, microwave thermokeratoplasty may employ a near field microwave applicator to apply energy to the cornea and raise the corneal temperature. At about 60° C., the collagen fibers in the cornea shrink. The onset of shrinkage is rapid, and stresses resulting from this shrinkage reshape the corneal surface. Thus, application of heat energy according to particular patterns, including, but not limited to, circular or annular patterns, may cause aspects of the cornea to flatten and improve vision in the eye.

SUMMARY OF THE INVENTION

Embodiments according to aspects of the present invention provide systems and methods for stabilizing corneal tissue and improving its biomechanical strength after desired structural changes have been achieved in the corneal tissue. For example, the embodiments help to preserve the desired reshaping of the cornea produced by the application of thermokeratoplasty.

Accordingly, in some embodiments, heat is generated in corneal fibrils in a cornea of an eye according to a selected pattern. The heat causes the corneal fibrils corresponding to the selected pattern to transition from a first structure to a second structure. The second structure provides a reshaping of the cornea. A cross-linking agent is then activated in the region of corneal fibrils according to the selected pattern. The cross-linking agent prevents the corneal fibrils from changing from the second structure. In some embodiments, the cross-linking agent is applied according to the selected pattern. In other embodiments, an initiating element that activates the cross-linking agent may be applied to the treated corneal fibrils according to the selected pattern.

Some embodiments provide a system that includes a source of a cross-linking agent or an initiating element. The cross-linking agent preserves structural changes in corneal fibrils generated by an application of heat to an eye, and the initiating element activates cross-linking activity in the corneal fibrils. The system also includes a delivery device positionable between the source and the eye. The delivery device defines a selected pattern and delivers the cross-linking agent or the initiating element to corneal fibrils according to the selected pattern. For example, the initiating element may be ultraviolet light. In some embodiments, the delivery device may be a mask that blocks the ultraviolet light according to the selected pattern. In other embodiments, the delivery device may be an optical device that redirects the ultraviolet light from the source to define the pattern. In a particular embodiment, the delivery device may be an axicon that receives the ultraviolet light from the source as a collimated beam and transforms the collimated beam into an annulus of light.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 1 illustrates an example system for applying heat to a cornea of an eye to cause reshaping of the cornea.

FIG. 2B illustrates another high resolution images of the cornea of FIG. 2A.

FIG. 3A illustrates an example approach for stabilizing changes in corneal structure induced by the application of energy according to aspects of the present invention.

FIG. 3B illustrates another example approach for stabilizing changes in corneal structure induced by the application of energy according to aspects of the present invention.

DETAILED DESCRIPTION

Figure 2A:
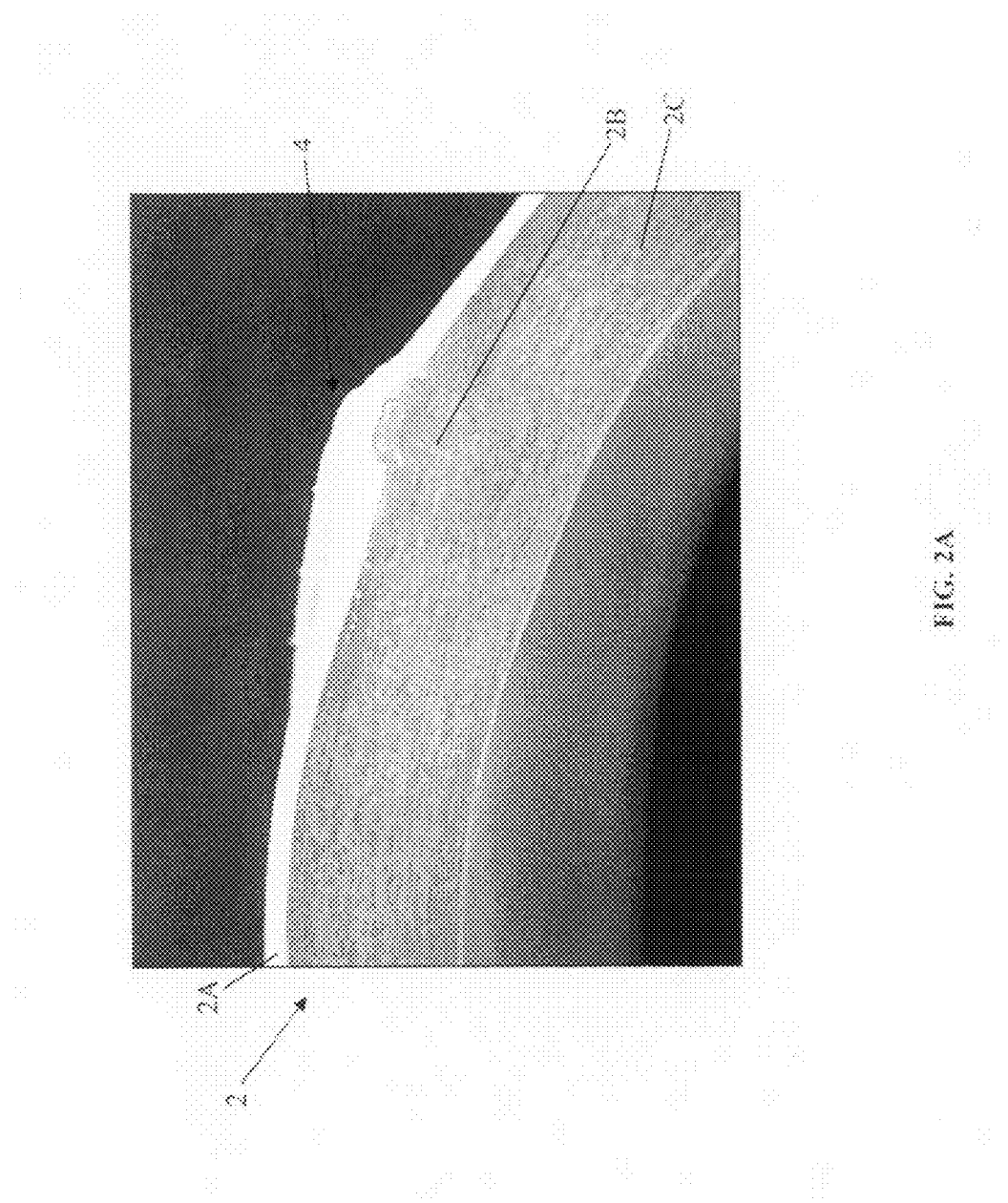
FIG. 2A illustrates a high resolution image of a cornea after heat has been applied.

FIG. 1 illustrates an example system for applying energy to a cornea 2 of an eye 1 to generate heat and cause reshaping of the cornea. In particular, FIG. 1 shows an applicator 110 with an electrical energy conducting element 111 that is operably connected to an electrical energy source 120, for example, via conventional conducting cables. The electrical energy conducting element 111 extends from a proximal end 110A to a distal end 110B of the applicator 110. The electrical energy conducting element 111 conducts electrical energy from the source 120 to the distal end 110B to apply heat energy to the cornea 2, which is positioned at the distal end 110B. In particular, the electrical energy source 120 may include a microwave oscillator for generating microwave energy. For example, the oscillator may operate at a microwave frequency range of 400 MHz to 3000 MHz, and more specifically at a frequency of around 915 MHz or 2450 MHz which has been safely used in other applications. As used herein, the term "microwave" may generally correspond to a frequency range from about 10 MHz to about 10 GHz.

As further illustrated in FIG. 1, the electrical energy conducting element 111 may include two microwave conductors 111A and 111B, which extend from the proximal end 110A to the distal end 110B of the applicator 110. In particular, the conductor 111A may be a substantially cylindrical outer conductor, while the conductor 111B may be a substantially cylindrical inner conductor that extends through an inner passage extending through the conductor 111A. With the inner passage, the conductor 111A has a substantially tubular shape. The inner and the outer conductors 111A and 111B may be formed, for example, of aluminum, stainless steel, brass, copper, other metals, coated metals, metal-coated plastic, or any other suitable conductive material.

With the concentric arrangement of conductors 111A and 111B, a substantially annular gap 111C of a selected distance is defined between the conductors 111A and 111B. The annular gap 111C extends from the proximal end 110A to the distal end 110B. A dielectric material 111D may be used in portions of the annular gap 111C to separate the conductors 111A and 111B. The distance of the annular gap 111C between conductors 111A and 111B determines the penetration depth of microwave energy into the cornea 2 according to established microwave field theory. Thus, the energy conducting element 111 receives, at the proximal end 110A, the electrical energy generated by the electrical energy source 120, and directs microwave energy to the distal end 111B, where the cornea 2 is positioned.

In general, the outer diameter of the inner conductor 111B may be selected to achieve an appropriate change in corneal shape, i.e. keratometry, induced by the exposure to microwave energy. Meanwhile, the inner diameter of the outer conductor 111A may be selected to achieve a desired gap between the conductors 111A and 111B. For example, the outer diameter of the inner conductor 111B ranges from about 2 mm to about 10 mm while the inner diameter of the outer conductor 111A ranges from about 2.1 mm to about 12 mm. In some systems, the annular gap 111C may be sufficiently small, e.g., in a range of about 0.1 mm to about 2.0 mm, to minimize exposure of the endothelial layer of the cornea (posterior surface) to elevated temperatures during the application of energy by the applicator 110.

A controller 140 may be employed to selectively apply the energy any number of times according to any predetermined or calculated sequence. In addition, the heat may be applied for any length of time. Furthermore, the magnitude of heat being applied may also be varied. Adjusting such parameters for the application of heat determines the extent of changes that are brought about within the cornea 2. Of course, the system attempts to limit the changes in the cornea 2 to an appropriate amount of shrinkage of collagen fibrils in a selected region and according to a selected pattern. When employing microwave energy to generate heat in the cornea 2, for example with the applicator 110, the microwave energy may be applied with low power (of the order of 40 W) and in long pulse lengths (of the order of one second). However, other systems may apply the microwave energy in short pulses. In particular, it may be advantageous to apply the microwave energy with durations that are shorter than the thermal diffusion time in the cornea. For example, the microwave energy may be applied in pulses having a higher power in the range of 500 W to 3 KW and a pulse duration in the range of about 10 milliseconds to about one second.

Referring again to FIG. 1, at least a portion of each of the conductors 111A and 111B may be covered with an electrical insulator to minimize the concentration of electrical current in the area of contact between the corneal surface (epithelium) 2A and the conductors 111A and 111B. In some systems, the conductors 111A and 111B, or at least a portion thereof, may be coated with a material that can function both as an electrical insulator as well as a thermal conductor. A dielectric layer 110D may be employed along the distal end 111B of the applicator 110 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibrils in a mid-depth region 2B of the cornea 2. Accordingly, the dielectric layer 110D is positioned between the conductors 111A and 111B and the cornea 2. The dielectric layer 110D may be sufficiently thin to minimize interference with microwave emissions and thick enough to prevent superficial deposition of electrical energy by flow of conduction current. For example, the dielectric layer 110D may be a biocompatible material deposited to a thickness of about 0.002 inches. In general, an interposing layer, such as the dielectric layer 110D, may be employed between the conductors 111A and 111B and the cornea 2 as long as the interposing layer does not substantially interfere with the strength and penetration of the microwave radiation field in the cornea 2 and does not prevent sufficient penetration of the microwave field and generation of a desired heating pattern in the cornea 2. The dielectric material may be elastic, such as polyurethane and silastic, or nonelastic, such as Teflon® and polyimides. The dielectric material may have a fixed dielectric constant or varying dielectric constant by mixing materials or doping the sheet, the variable dielectric being spatially distributed so that it may affect the microwave hearing pattern in a customized way. The thermal conductivity of the material may have fixed thermal properties (thermal conductivity or specific heat), or may also vary spatially, through mixing of materials or doping, and thus provide a means to alter the heating pattern in a prescribed manner. Another approach for spatially changing the heating pattern is to make the dielectric sheet material of variable thickness. The thicker region will heat less than the thinner region and provides a further means of spatial distribution of microwave heating.

During operation, the distal end 110B of the applicator 110 as shown in FIG. 1 is positioned on or near the corneal surface 2A. Preferably, the applicator 110 makes direct contact with the corneal surface 2A. In particular, such direct contact positions the conductors 111A and 111B at the corneal surface 2A (or substantially near the corneal surface 2A if there is a thin interposing layer between the conductors 111A and 111B and the corneal surface 2A). Accordingly, direct contact helps ensure that the pattern of microwave heating in the corneal tissue has substantially the same shape and dimension as the gap 111C between the two microwave conductors 111A and 111B.

The system of FIG. 1 is provided for illustrative purposes only, and other systems may be employed to apply heat to cause reshaping of the cornea. Other systems are described, for example, in U.S. patent application Ser. No. 12/208,963, filed Sep. 11, 2008, which is a continuation-in-part application of U.S. patent application Ser. No. 11/898,189, filed on Sep. 10, 2007, the contents of these applications being entirely incorporated herein by reference. As described in U.S. patent application Ser. No. 12/208,963, a cooling system may also be employed in combination with the applicator 110 to apply coolant to the cornea 2 and determine how the energy is applied to the cornea 2.

FIGS. 2A-D illustrate an example of the effect of applying heat to corneal tissue with a system for applying heat, such as the system illustrated in FIG. 1. In particular, FIGS. 2A and 2B illustrate high resolution images of cornea 2 after heat has been applied. As FIGS. 2A and 2B show, a lesion 4 extends from the corneal surface 2A to a mid-depth region 2B in the corneal stroma 2C. The lesion 4 is the result of changes in corneal structure induced by the application of heat as described above. These changes in structure result in an overall reshaping of the cornea 2. It is noted that the application of heat, however, has not resulted in any heat-related damage to the corneal tissue.

Figure 2C:
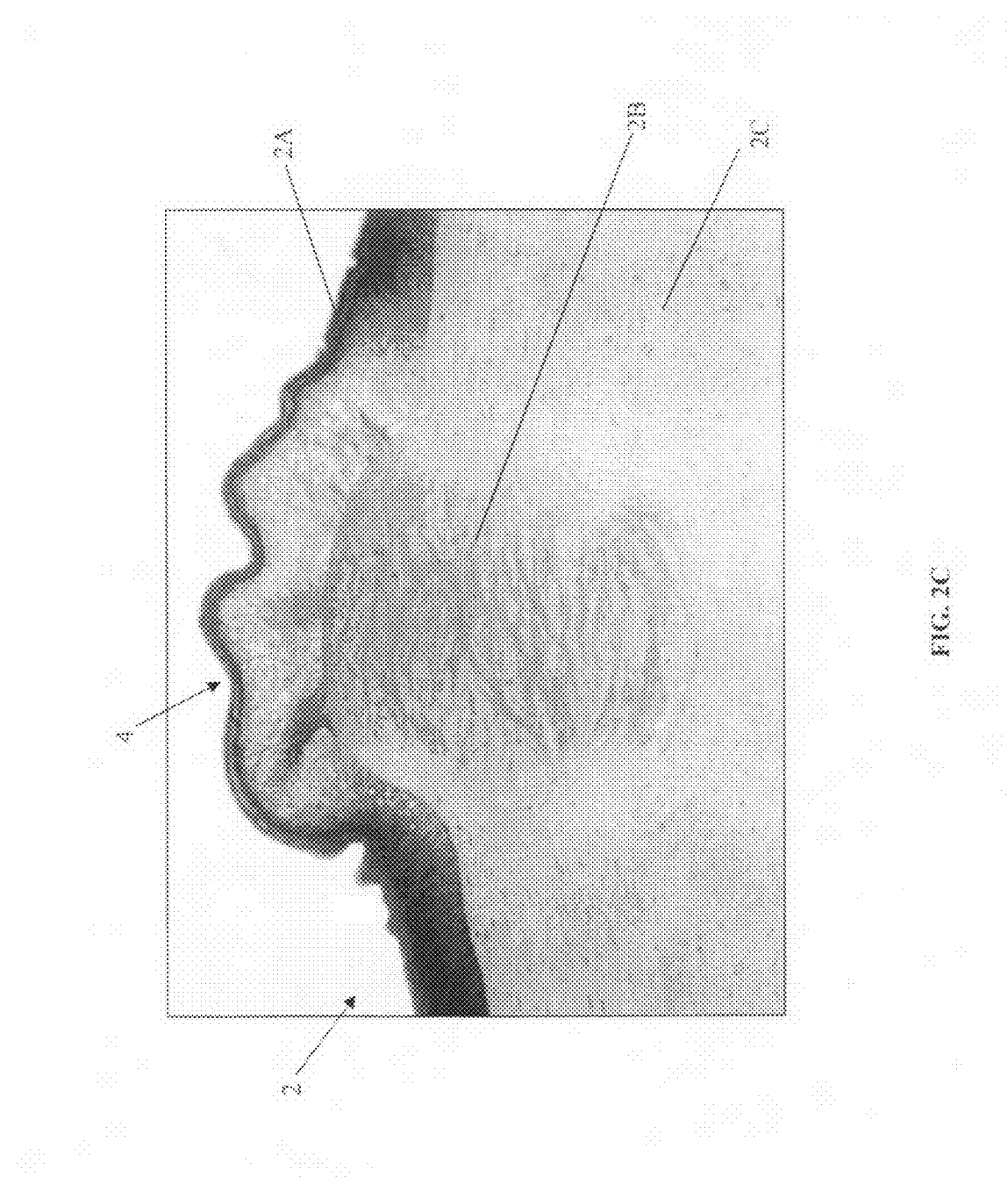
FIG. 2C illustrates a histology image of the cornea of FIG. 2A.
Figure 2D:
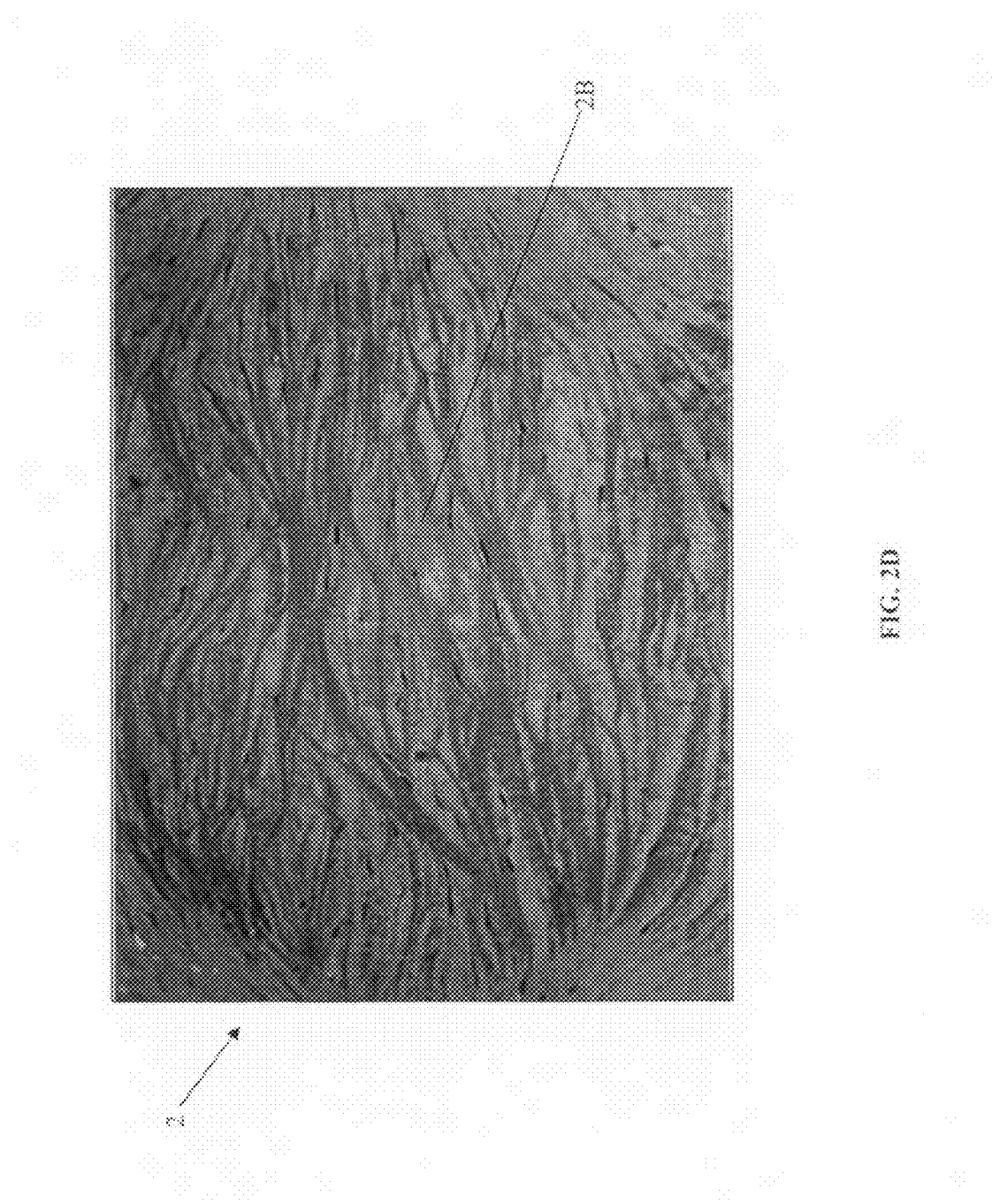
FIG. 2D illustrates another histology image of the cornea of FIG. 2A.

As further illustrated in FIGS. 2A and 2B, the changes in corneal structure are localized and limited to an area and a depth specifically determined by an applicator as described above. FIGS. 2C and 2D illustrate histology images in which the tissue shown in FIGS. 2A and 2B has been stained to highlight the structural changes induced by the heat. In particular, the difference between the structure of collagen fibrils in the mid-depth region 2B where heat has penetrated and the structure of collagen fibrils outside the region 2B is clearly visible. Thus, the collagen fibrils outside the region 2B remain generally unaffected by the application of heat, while the collagen fibrils inside the region 2B have been rearranged and formed new bonds to create completely different structures. In other words, unlike processes, such as orthokeratology, which compress areas of the cornea to reshape the cornea via mechanical deformation, the collagen fibrils in the region 2B are in an entirely new state.

In sum, energy is applied to a cornea through an applicator, such as the applicator 110 shown in FIG. 1, to generate heat that produces a desired reshaping of the cornea. Although the heat induces structural changes in the collagen fibrils of the cornea, the desired effects of reshaping the cornea may be mitigated or reversed at least partially if the collagen fibrils continue to change after the desired reshaping has been achieved. Therefore, aspects of the present invention provide approaches for preserving the desired corneal structure and reshaping that result from the application of heat. In particular, embodiments may provide approaches for initiating molecular cross-linking of the corneal collagen to stabilize the corneal tissue and improve its biomechanical strength after the desired shape change has been achieved. For example, cross-linking may be induced in the corneal stroma 2C at the lesion 4 formed by the application of heat as shown in FIGS. 2A-C.

Referring to FIG. 3A, an example embodiment 300A according to aspects of the present invention is illustrated. Specifically, in step 310, energy is applied to corneal tissue to generate heat-induced structural changes and a desired shape change, as described previously. In step 320, the changed corneal tissue is treated with a cross-linking agent 322. The cross-linking agent 322 is then activated in step 330 with an initiating element 332. Activation of the cross-linking agent 322, for example, may be triggered thermally by the application of microwaves or light.

As the example embodiment 300B of FIG. 3B shows further, Ribloflavin may be applied topically as a cross-linking agent 322' to the changed corneal tissue in step 320, and ultraviolet (UV) light may be applied as an initiating element 332' in step 330 to initiate cross-linking in the corneal areas treated with Ribloflavin. Specifically, the UV light initiates cross-linking activity by activating the applied Riboflavin to release reactive oxygen radicals in the corneal tissue.

A technique for inducing corneal cross-linking may require removing the epithelium across the entire corneal surface prior to applying the Ribloflavin topically to the corneal stroma. This technique is applied to the entire surface of the cornea. In addition, this technique typically requires debridement of the epithelium to allow the cross-linking agent to enter the stroma and to allow the UV light to hit the stroma and activate the agent. Debridement of the epithelium promotes delivery of the cross-linking agent and the UV light to the stroma as the epithelium may act at least as a partial barrier. Although this technique may indeed initiate cross-linking in the stroma, this technique may also be accompanied by undesirable effects. In particular, broad application of the cross-linking agent may induce stiffening of the corneal tissue and may cause unpredictable refractive results across the entire cornea.

According to aspects of the present invention, however, embodiments may not apply the cross-linking agent and the activating UV light across the entire cornea. Rather, the cross-linking agent is initiated in a smaller portion of the cornea corresponding, for example, at the site of the lesion 4 shown in FIGS. 2A-C. Indeed, when the applicator 110 described previously is applied to the cornea 2, the energy is applied according to a pattern defined by the shape of the energy conducting element 111 at the distal end 110B. Correspondingly, the cornea 2 only experiences structural changes in areas that correspond to the shape of the energy conducting element 111. As such, the embodiments only require application of the cross-linking agent to the limited areas of the cornea 2 that experience the desired structural change. By applying the cross-linking agent according to a controlled pattern, the embodiments achieve more precise cross-linking activity and minimize the unpredictable refractive changes that may occur with broader application of the cross-linking agent.

Accordingly, referring to the embodiment 300B of FIG. 3B, embodiments employ a patterned removal of the epithelium in step 315 before applying the cross-linking agent 322', i.e., Riboflavin, in step 320 and the initiating element 332', i.e., UV light, in step 330. Rather than a broad removal of the epithelium from across the entire cornea, embodiments only remove the epithelium in specific areas of the cornea where structural changes have been induced according to a desired pattern. Advantageously, limiting removal of the epithelium to a smaller area also results in less post-operative pain for the patient, reduces the healing period, and minimizes other complications associated with the removal of the epithelium.

Although the epithelium may provide at least a partial barrier to the initiation of cross-linking in areas where the epithelium has not been removed, embodiments may apply a mask to ensure that cross-linking activity is limited to desired areas of the cornea. As illustrated in the system 400 in FIG. 4A, a mask 410 may be positioned over the corneal surface 2A before the initiating element 332, i.e., the UV light, from a source 331 is applied. FIG. 4B illustrates an example pattern 414 for the mask 410. In particular, the mask 410 may be a device similar to a contact lens that is approximately 5 mm in diameter. As described previously, the energy conducting element 111 of the applicator 110 shown in FIG. 1 employs two concentric conductors 111A and 111B that apply energy to the cornea in a pattern that corresponds to the annular gap 111C between them. As such, the areas of resulting structural changes in the cornea 2 correspond to this annular pattern. To stabilize these structural changes, cross-linking generally only needs to be initiated along the annular pattern of the structural changes. As a result, the mask 410 of FIG. 3 only allows UV light from the source 331 to pass to the cornea 2 and the cross-linking agent, e.g., Riboflavin, is activated according to the annular pattern 414. In particular, a UV-blocking material 412 defines the pattern 414 on the mask 410. In alternative embodiments, the pattern 414 may be structurally defined as a cut-out from the mask 410. In any case, any UV light from the source 331 outside this pattern 414 is blocked by the mask 410. Accordingly, the mask 410 provides more precise activation of the cross-linking agent.

Figure 3C:
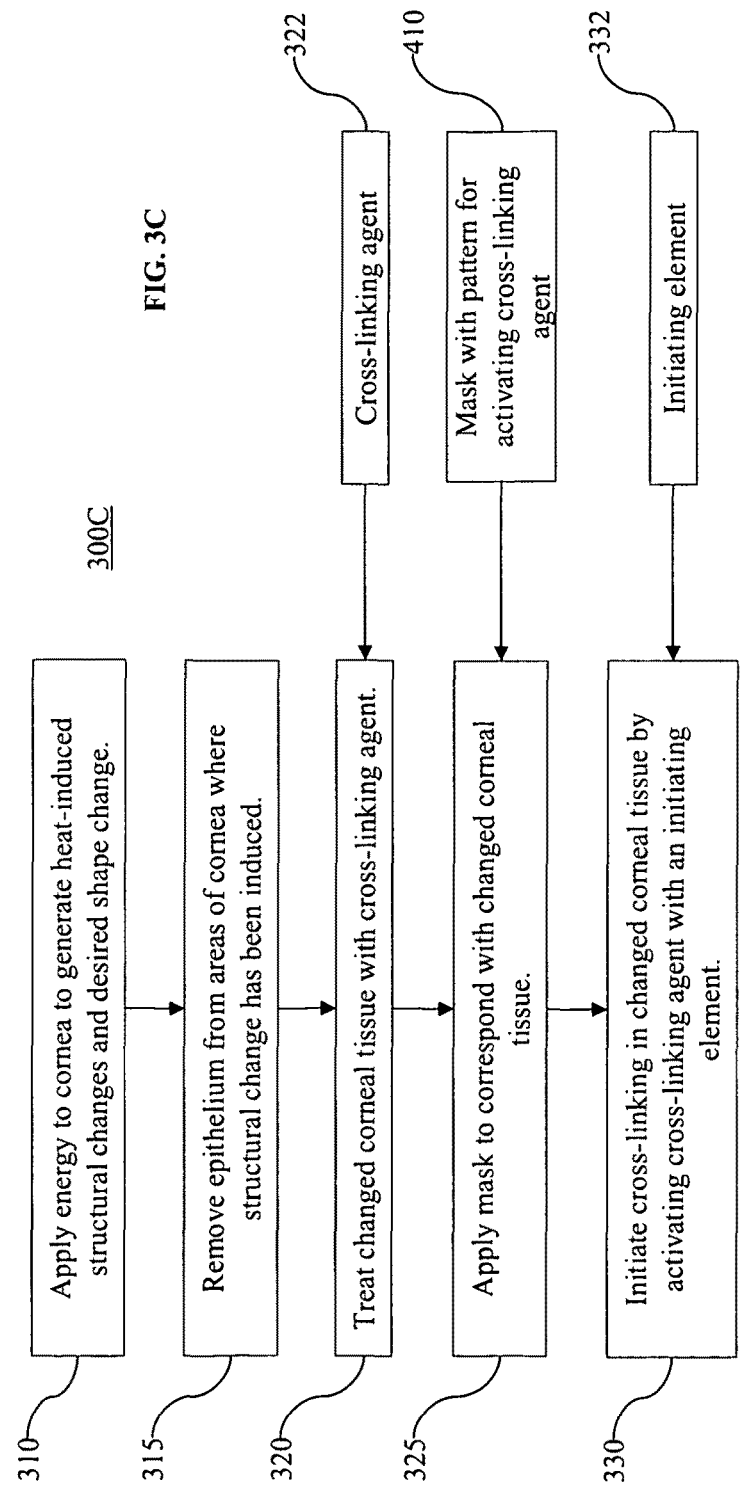
FIG. 3C illustrates yet another example approach for stabilizing changes in corneal structure induced by the application of energy according to aspects of the present invention.
Figure 3D:
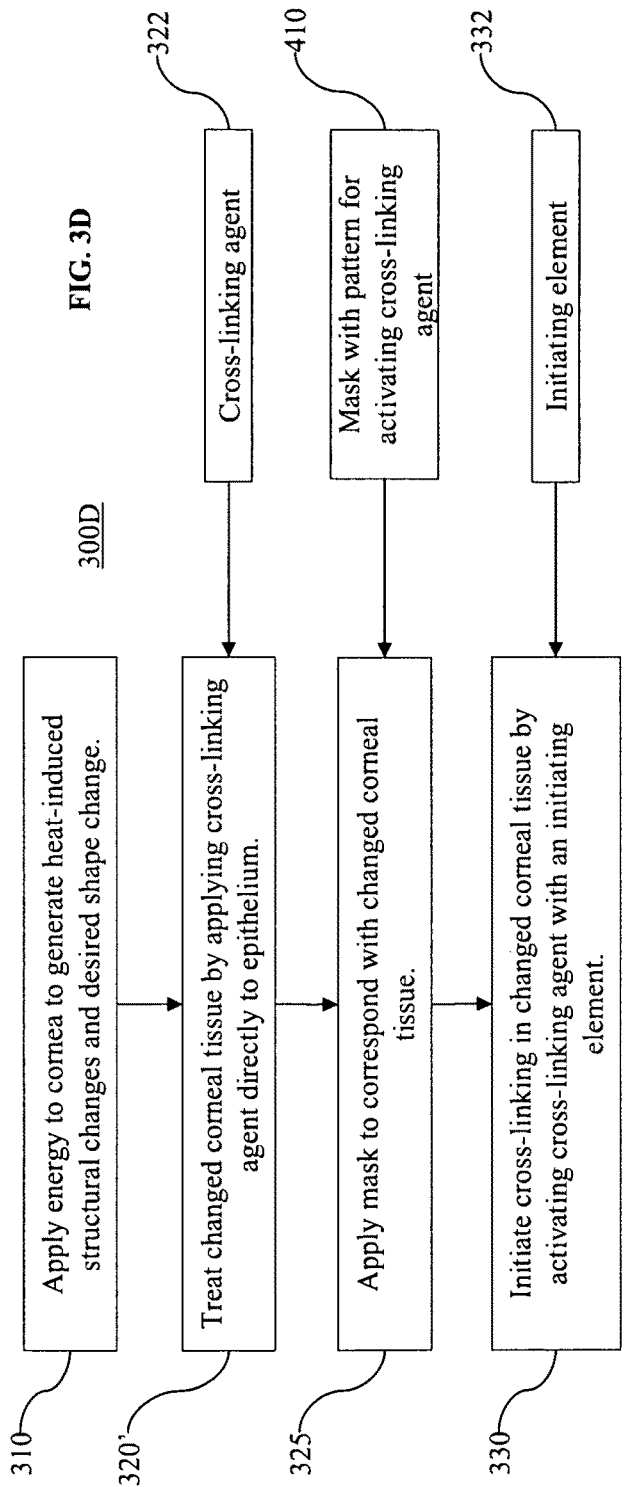
FIG. 3D illustrates a further example approach for stabilizing changes in corneal structure induced by the application of energy according to aspects of the present invention.
Figure 4B:
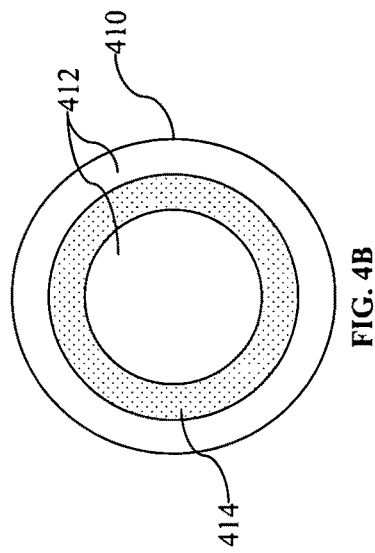
FIG. 4B illustrates an example initiation pattern for the mask of FIG. 4A.

Thus, in the example embodiment of 300C of FIG. 3C, a mask 410 is applied to the eye in step 325 after the limited pattern of the epithelium is removed in step 315 and a cross-linking agent 322, e.g., Riboflavin, is applied in step 320 to the area where the epithelium has been removed. Once the cross-linking agent 322 has been effectively applied to the stroma, the mask 410 that determines more precisely where in the stroma the applied Riblofavin should be activated. Thus, in step 330, the initiating element 332, e.g., UV light, is applied to the eye to initiate cross-linking according to a pattern in the mask 410.

Although cross-linking agents, such as Riboflavin, may be effectively applied to the stroma by removing the overlying epithelium before application, it has been shown that cross-linking agents can chemically transition across the epithelium into the stroma. Indeed, Riboflavin may also be delivered to the stroma by applying it topically on the epithelium. Accordingly, in the embodiment 300D shown in FIG. 3D, no removal of the epithelium is required. Moreover, in some cases, the epithelium may be treated to promote the transition of the cross-linking agent through the epithelium. Accordingly, in step 320', the cross-linking agent may be applied directly to the epithelium. With the appropriate delivery of the cross-linking agent to the stroma, a mask 410 is applied to the eye in step 325 and the initiating element 332 is delivered in step 330 to initiate cross-linking according to the pattern in the mask 410. Advantageously, the embodiment 300D of FIG. 3D eliminates the post-operative pain, healing period, and other complications associated with the removal of the epithelium.

Although the mask 410 is employed to deliver the initiating element 332 to the cornea according to a particular pattern, masks may also be employed in some embodiments to deliver the cross-linking agent according to the specific pattern. Thus, the source 331 of the initiating element shown in FIG. 4A would be replaced by a source of the cross-linking agent.

Figure 4A:
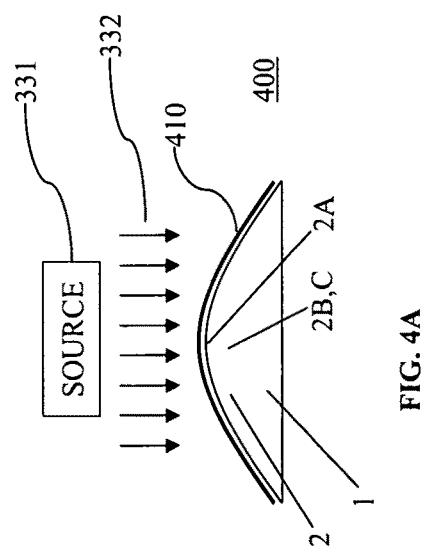
FIG. 4A illustrates an example system that employs a mask to initiate cross-linking in corneal tissue after the application of energy according to aspects of the present invention.
Figure 5B:
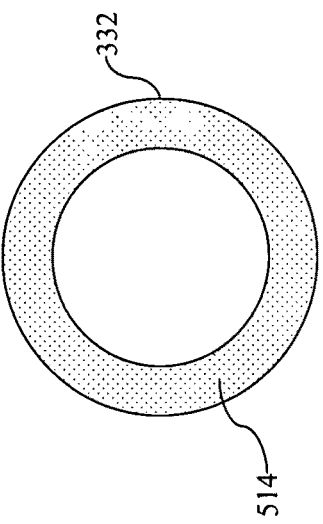
FIG. 5B illustrates an example initiation pattern corresponding to the optical device of FIG. 5A.
Figure 5A:
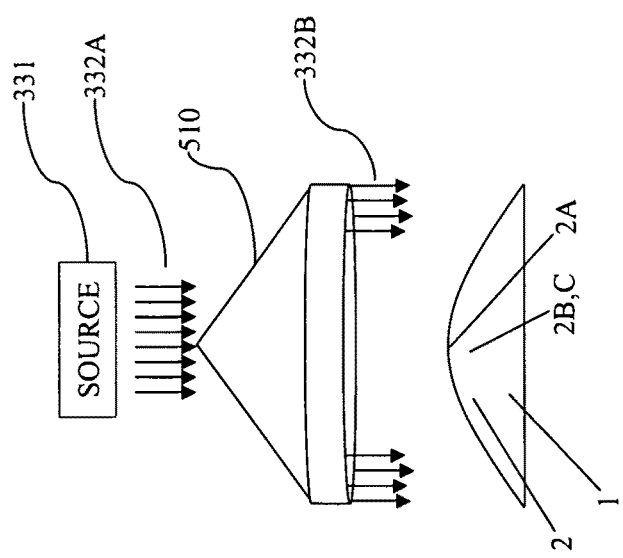
FIG. 5A illustrates an example system that employs an optical device to initiate cross-linking in corneal tissue after the application of energy according to aspects of the present invention.

Moreover, although the system 400 may employ a mask 410, the devices employed for patterned initiation of a cross-linking agent is not limited to the use of such masks. Embodiments include more general systems and methods that activate a cross-linking agent according to a precise pattern, regardless of the type of device that actually directs the initiating element to specific areas of the cornea. For example, as shown in FIG. 5A, a system 500 transforms the initiating element 332A, e.g., UV light, from a source 331 to define a desired pattern 514 as shown in FIG. 5B. In contrast to the system 400, the system 500 does not block the initiating element 332 from a source 331 from reaching areas outside a pattern. As illustrated in FIG. 5A, an optical device, such as an axicon 510, receives UV light as a collimated beam 332A from the source 331 and transforms the collimated beam 332A into an annulus of light 332B. The annulus 332B thus delivers the UV light to the cornea 2 according to an annular pattern 514 that corresponds to the structural changes that are induced, for example, by the applicator 110 described previously. In other words, the pattern 514 matches the areas where initiation of the cross-linking agent is desired. In general, any number or types of optical devices, such as lenses, beam-splitters, and the like, may be employed to achieve the desired shape for delivering an initiating element. Moreover, in some embodiments, the use of a mask as illustrated in FIG. 4A may be combined with the use of an optical device.

Figure 6:
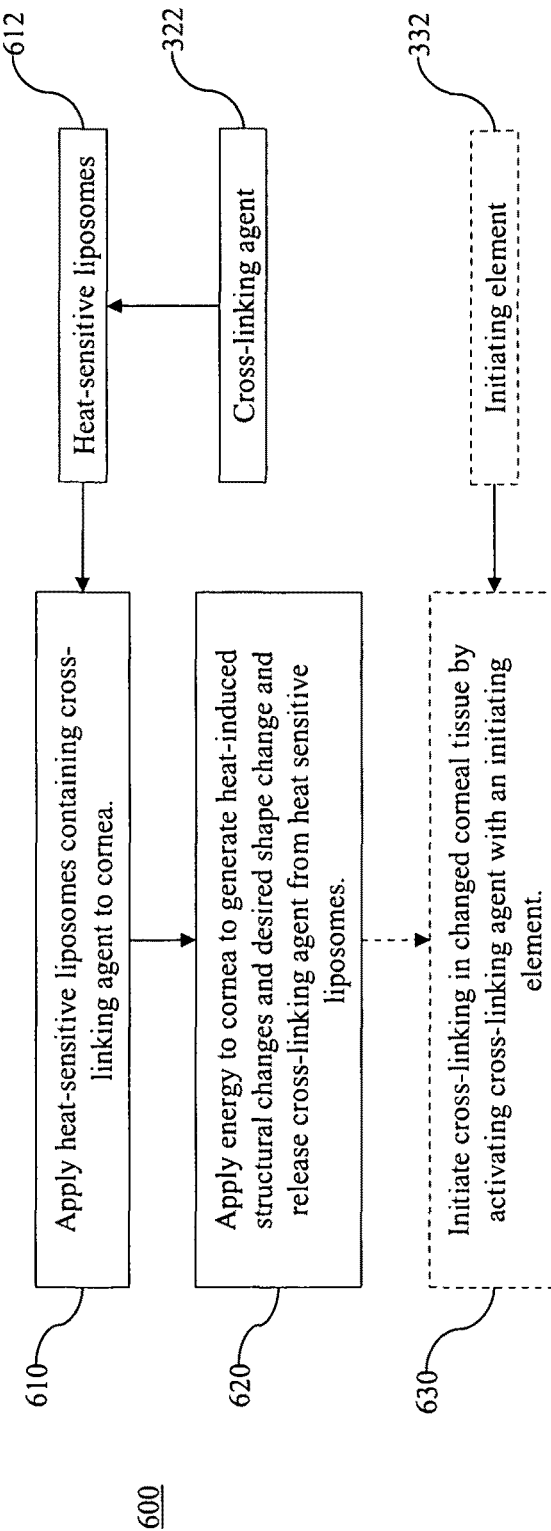
FIG. 6 illustrates another approach for stabilizing changes in corneal structure induced by the application of energy according to aspects of the present invention.

Although the embodiments described previously may apply the cross-linking element, such as Riboflavin, directly to the cornea, some embodiments may employ other techniques to deliver the cross-linking agent to the cornea. For example, as shown in the example embodiment 600 of FIG. 6, heat-sensitive liposomes 612, whose contents include a cross-linking agent 622, are applied in step 610 onto the treatment site of the cornea. In particular, the heat-sensitive liposomes are applied onto the area where the heat is generally to be applied for reshaping the cornea. In step 620, heat is applied to the cornea, for example, with the applicator 110 above. As described previously, the heat causes structural changes in the cornea. However, because the heat sensitive liposomes 612 have also been applied to the cornea, the heat from the applicator also causes the cross-linking agent 622 to be released from the heat sensitive liposomes 612. The heat is applied to the cornea in a desired pattern to produce the desired reshaping, so only the heat sensitive liposomes 612 in the area of this pattern are activated by heat and release the cross-linking agent 322. Thus, only the areas of structural change, i.e., where heat is applied, are exposed to the cross-linking agent 622. Like other embodiments described herein, the cross-linking agent 622 is applied to limited areas where stabilization of changes to corneal structure is desired. As shown in FIG. 6, if further activation of the cross-linking agent 322 is required, the initiating element 332 may be subsequently applied in step 630 according to the techniques described herein. Although embodiments described herein may employ an initiating element, other embodiments may not require an initiating element. In the embodiment of FIG. 6, the pattern for cross-linking activity is be achieved by a patterned delivery of the cross-linking agent 322 via heat-sensitive liposomes 612, rather than a patterned delivery of an initiating element 332.

In alternative embodiments, cross-linking agents may be delivered with heat sensitive liposomes, but the heat that activates the heat sensitive liposomes does not have to coincide with the heat that causes the reshaping of the cornea. For example, the heat sensitive liposomes may be applied after the cornea is reshaped and a second application of heat may be applied to release the cross-linking agent. In some cases, the second application of heat does not cause shape changes to the cornea. In other cases, the second application of heat may cause supplemental (desired) changes to the corneal shape. As before, the application of heat may be applied in a specific pattern to limit the application of the cross-linking agent to areas where stabilization of structural changes in the cornea is desired.

Although the embodiments described herein may initiate cross-linking in the cornea according to an annular pattern defined by an applicator such as the applicator 110 of FIG. 1, the initiation pattern in other embodiments is not limited to a particular shape. Indeed, energy may be applied to the cornea in non-annular patterns, so cross-linking may be initiated in areas of the cornea that correspond to the resulting non-annular changes in corneal structure. Examples of the non-annular shapes by which energy may be applied to the cornea are described in U.S. patent Ser. No. 12/113,672, filed on May 1, 2008, the contents of which are entirely incorporated herein by reference.

The use of Riboflavin as the cross-linking agent and UV light as an initiating element in the embodiments above is described for illustrative purposes only. In general, other types of cross-linking agents may be employed according to aspects of the present invention. For example, to provide the required combination of optical transparency and mechanical resilience for corneal function, the cornea employs an extracellular matrix containing collagen fibrils that are spaced and organized uniformly into orthogonal sheets. Fibril associated collagens with interrupted triple helices (FACIT collagens) and leucine-rich repeat (LRR) proteoglycans are natural binding macromolecules that have important roles in determining the structure and function of collagen fibrils. FACIT collagens that occur in the cornea include, for example, type VI, XII, and XIV collagens. Meanwhile, LRR proteoglycans that occur in the cornea include decorin, lumican, keratocan, and osteoglycin. FACIT collagens and LRR proteoglycans cross-link with collagen fibrils and control fibril diameter. In addition, these macromolecules may form bridges between fibrils and provide an inter-fibril bonding that limits relative movement between the fibrils while enabling some flexibility. Due to their ability to bind fibrils together, FACIT collagens and LRR proteoglycans may thus be used as components of the cross-linking agents applied according to aspects of the present invention.

In some embodiments, the cross-linking agent may be provided as an ophthalmic preparation that facilitates application to the corneal surface and allows sufficient delivery of the cross-linking agent to the target corneal fibrils below the epithelium. For example, a concentration of FACIT collagen and/or LRR proteoglycan may be dissolved in a physiologically compatible buffer solution, such as a phosphate buffer, to create the composition. The corresponding concentration in the solution may be approximately 10 µg/ml to 500 µg/ml.

Alternatively, the cross-linking agent may be selectively applied as an ophthalmic ointment with a petrolatum base, for example. To facilitate the delivery of the shape retention substance to the regions undergoing structural change below the corneal surface, e.g., the mid-depth region 2B, the pH of the cross-linking agent may be adjusted to an appropriate value, e.g. approximately 7.6 to 8.0, to open up the collagen matrix structure. As described previously, the cross-linking agent may be applied to cornea according to a specific pattern that corresponds to the areas of changes to the corneal structure. For example, a mask, similar to the mask 410 discussed previously, may be employed to deliver the cross-linking agent according to the specific pattern.

In addition, the cross-linking agent may be applied before and/or after the delivery of heat to the cornea. The length of time for the application depends on the cross-linking agent. If the cross-linking agent is applied before the heat is delivered, more heat may have to be delivered to overcome any resistance to fibril movement that results from the application of the shape retention substance. In the end, however, the presence of the FACIT collagen and/or LRR proteoglycan, for example, delivered with the cross-linking agent helps maintain the structural changes induced by the heat, whether the cross-linking agent is applied before and/or after the heat. It is noted that application of the cross-linking agent in embodiments of the present invention is intended to preserve a new structural arrangement of corneal fibrils, and does not maintain a mechanical deformation that is imposed onto a corneal structure which remains unchanged during treatments such as orthokeratology. Indeed, any process of reshaping the cornea through mechanical deformation would likely eschew the application of the shape retention substance before the forces are applied, as the corneal structure would resist deformation and the process would have to be applied for a longer time or be rendered ineffective. On the other hand, the application of heat may be more easily adjusted to overcome any such resistance.

While the present invention has been described in connection with a number of exemplary embodiments, and implementations, the present inventions are not so limited, but rather cover various modifications, and equivalent arrangements.

What is claimed is:

1. A method for applying therapy to an eye, comprising:
generating heat to corneal fibrils in a cornea of an eye according to a selected pattern, the heat causing the corneal fibrils corresponding to the selected pattern to transition from a first structure to a second structure, the second structure providing a reshaping of the cornea; and
activating a cross-linking agent in the region of corneal fibrils according to the selected pattern, the cross-linking agent preventing the corneal fibrils from changing from the second structure.

2. The method according to claim 1, further comprising applying the cross-linking agent in the region of corneal fibrils according to the selected pattern.

3. The method according to claim 2, wherein applying the cross-linking agent according to the selected pattern comprises removing corneal epithelium according to the selected pattern and applying the cross-linking agent directly to the region of corneal fibrils below the epithelium.

4. The method according to claim 3, wherein the initiating element comprises ultraviolet light.

5. The method according to claim 3, wherein applying the initiating element according to the selected pattern comprises applying a mask, the mask limiting application of the initiating element according to the selected pattern.

6. The method according to claim 3, wherein applying the initiating element according to the selected pattern comprises applying at least one optical device, the at least one optical device directing the initiating element to the eye according to the selected pattern.

7. The method according to claim 3, wherein the cross-linking agent is Riboflavin.

8. The method according to claim 1, wherein activating the cross-linking agent according to the selected pattern comprises applying an initiating element to the region of the corneal fibrils according to the selected pattern, the initiating element activating the cross-linking agent.

9. The method according to claim 1, further comprising before the step of generating the heat, applying the cross-linking agent in the region of corneal fibrils.

10. The method according to claim 1, further comprising applying heat-sensitive liposomes containing the cross-linking agent to the region of corneal fibrils.

11. The method according to claim 1, wherein the step of applying the heat-sensitive liposomes occurs before the step of generating the heat, the heat causing release of the cross-linking agent from the heat-sensitive liposomes.

12. The method according to claim 1, wherein the cross-linking agent comprises at least one of fibril associated collagens with interrupted triple helices (FACIT collagens) and leucine-rich repeat (LRR) proteoglycans.

13. The method according to claim 1, wherein the cross-linking agent is in an ophthalmic solution or an ophthalmic ointment.

\* \* \* \* \*